United States Patent [19]

Stuemke et al.

[11] Patent Number: 5,094,689

[45] Date of Patent: Mar. 10, 1992

[54] GOLD-BEARING PREPARATION FOR THE PRODUCTION OF HIGHLY POROUS COATINGS

[75] Inventors: Manfred Stuemke; Harry Schiwiora, both of Pforzheim, Fed. Rep. of Germany

[73] Assignee: Degussa Aktiengesellschaft, Frankfurt, Fed. Rep. of Germany

[21] Appl. No.: 634,491

[22] Filed: Dec. 27, 1990

[30] Foreign Application Priority Data

Jan. 8, 1990 [DE] Fed. Rep. of Germany ....... 4000302

[51] Int. Cl.$^5$ .............................................. C09K 3/00
[52] U.S. Cl. .................................. 106/35; 433/217.1; 433/222.1; 433/228.1
[58] Field of Search ................. 106/35, 1.13; 433/206, 433/222.1

[56] References Cited

U.S. PATENT DOCUMENTS 4,369,068  6/1983  Hausselt et al. .................... 106/1.18
4,468,251  8/1984  Hausselt et al. .................... 106/1.18

Primary Examiner—William R. Dixon, Jr.
Assistant Examiner—Margaret V. Einsmann
Attorney, Agent, or Firm—Beveridge DeGrandi & Weilacher

[57] ABSTRACT

Gold preparations are used for the production of highly porous coatings on metal surfaces by means of sintering. 1 to 10% by weight of a pore former is added to these gold preparations, the pore former comprises a material which suddenly decomposes or evaporates at 700° to 1050° C. and escapes from the layer without leaving a residue. Plastics and dental waxes in powder form are preferably used to this end.

8 Claims, No Drawings

GOLD-BEARING PREPARATION FOR THE PRODUCTION OF HIGHLY POROUS COATINGS

INTRODUCTION TO THE INVENTION

The present invention relates to a gold-bearing preparation for the production of ductile, highly porous coatings on metallic surfaces by means of sintering at 700° to 1050° C. The gold-bearing preparation is especially useful for the overlaying of metallic parts in dental technology. The gold-bearing preparation comprises 1 to 10% by weight of a pore former and 90 to 99% by weight of a mixture composed of 50 to 95% by weight gold powder and 5 to 50% by weight organic binder and solvent and optional additives of metal powders and/or ceramic powders.

In a composite of metallic parts with parts consisting of inorganic or organic materials, the shaping and the deformability of the border surfaces play an important part in the quality of the adhesion. A suitable surface profile with a high number of undercuts is striven for in order to obtain an intimate mechanical intermeshing of substratum and coating; compressible and/or ductile intermediate layers are advantageous for a force fit and for reducing mechanical tensions in the connection zone. Since an improved material composite expresses itself directly in a higher reliability of use and in a longer service life, there is a need for border surfaces prepared in this manner, especially in dental technology, e.g. for obtaining a compressible intermediate layer for the combination with other materials in order to prepare the surface of metallic parts which are to be fit in with low tension or adhered or veneered with plastic.

For example, DE-OS 37 41 847 describes a root pin which is provided with a porous, compressible layer of fine gold which can be compressed with a defined pressure by means of plastic deformation when the pin is inserted, thus producing a low-pressure, very tight contact to the root walls.

It is advantageous in the veneering of structures of dental prostheses, consisting of burn-on alloys, with dental ceramic masses, to use gold-bearing materials for the intermediate layers like those gold-bearing materials described e.g. in DE-OS 28 51 729, DE-OS 30 27 472 and DE-OS 30 27 473. The porosity which results in the intermediate layers when using these preparations is generally sufficient for a mechanical intermeshing of the cover layers and for buffering tensions. However, in individual instances, an even more extensive intermeshing of the material of the intermediate layer and the facing ceramics is necessary.

When structures of dental prostheses are faced with plastics, which is also used in dental technology, the formation of cracks and tears between the facing plastic and the metallic structure constitutes a basic problem for which the known preparations do not furnish any suitable intermediate layers from the standpoint of structure.

In addition to many suggestions made, e.g. the application of macro- or microretentions, coating with silanes, silicon dioxide or tin, DE-GM 82 07 485 describes a gold preparation mixed with ceramic particles. After the burning on between 950° C. and 1100° C., the ceramic component is subsequently dissolved out with hydrofluoric acid. However, the disadvantage is the high sintering temperature, which can not be tolerated by the alloys customarily used for plastic facing, as well as by the use of hydrofluoric acid necessary for dissolving out the oxide-ceramic components, which acid is known to be injurious to health.

Problems similar to those of a metal-plastic composite are also present in adhesive-bridge technology. Here too, an improved microretention of the adhesive layer on the metal structure results in a reduction of the failure rate. Whereas chemical or electrochemical etchings result only in a few heterogeneous base-metal alloys in suitable surface microstructures, a retentive intermediate layer on homogeneous and highly corrosion-resistant noble-metal alloys renders even these alloys suitable for adhesive-bridge technology.

Since only those intermediate-layer materials which exhibit a high corrosion resistance themselves are eligible for most applications, gold presents itself as the main component of such a material.

SUMMARY OF THE INVENTION

One object of the present invention was to solve the problem of developing a gold-bearing preparation for the production of ductile, highly porous coatings on metallic surfaces by means of sintering at 700° to 1050° C. The gold-bearing preparation is especially useful for the overlaying of metallic parts in dental technology. The gold-bearing preparation comprises 1 to 10% by weight of a pore former and 90 to 99% by weight of a mixture composed of 50 to 95% by weight gold powder and 5 to 50% by weight organic binders and solvents and optional additives of metal powders and/or ceramic powders which also result in a high adhesion for plastics.

DETAILED DESCRIPTION OF THE INVENTION

The above described problem is solved in that a powdery material is used as pore former which suddenly decomposes or evaporates at the sintering temperature and escapes without leaving a residue.

90 to 99% by weight of known preparations, like those described in DE-OS 30 27 472 and DE-OS 30 27 473, are added to 1 to 10% by weight of the pore former. It is preferable to use a plastic powder and/or wax powder which evaporates suddenly at 700° to 850° C. within a few milliseconds or which decomposes and escapes within 2 to 5 minutes from the layer without leaving a residue. Powders with a maximum particle size of 1 mm are especially suitable, and it has proven to be advantageous to use two powder fractions with 50 to 99% by weight exhibiting a size of up to 350 $\mu$m and 1 to 50% by weight a size between 350 and 800 $\mu$m. It is especially advantageous to add 65 to 75% by weight powder particles up to 350 $\mu$m and 25 to 35% by weight powder particles between 350 and 700 $\mu$m. Furthermore, it is advantageous to use spherical particles and to add 3 to 7% by weight of pore-former particles.

For example, polymethylmethacrylate particles can be used as plastic powder and dental-wax particles according to DIN 13 908 as wax powder.

By way of example, a mixture of 100 parts by weight of a preparation according to DE-OS 30 27 473 with 5 parts by weight of a dental-wax powder according to DIN 13 908 consisting of 70% spheres with diameters of up to 350 $\mu$m and of 30% spheres with diameters between 350 and 700 $\mu$m is sintered onto parts consisting of gold-palladium base alloys and silver-palladium base alloys at 700° to 850° C. for 2 to 5 minutes. Depending on the application, cohesive coatings with a thickness of 25 to 350 μm with a high number of predominantly open pores result without any recognizable influence on the type of alloy used as substrate.

Retentive gold coatings produced in this manner can be combined in a reliable, lasting manner not only with facing ceramics but also in particular with facing plastic. The resulting composite surprisingly exhibits such a great stability and tear resistance that in the case of one-sided plastic facings of alloy platelets, the latter are curved as a consequence of the polymerization shrinkage of the plastic and the plastic does not peel off from the platelets, as is otherwise the case. This unexpectedly stabile composite is still intact even after several weeks of storage in deionized water at room temperature, so that a considerable extension of the service life is achieved.

Further variations and modifications of the invention will become apparent to those skilled in the art from the foregoing and are intended to be encompassed by the claims appended hereto.

German Priority Application P 40 00 302.7-42 is relied on and incorporated by reference.

What is claimed:

1. A gold-bearing preparation for the production of ductile, highly porous coatings on metallic surfaces comprising 1 to 10% by weight of a pore former and 90 to 99% by weight of a mixture comprised of 50 to 95% by weight gold powder and 5 to 50% by weight of at least one member selected from the group consisting of organic binder, solvent, metal powders and ceramic powders; wherein said pore former is a wax powder which is capable of decomposing at a sintering temperature of 700°–850° C. and escaping without leaving a residue.

2. The gold-bearing preparation according to claim 1, wherein said pore former has a maximum particle size of 1 mm.

3. The gold-bearing preparation according to claim 2, wherein 50 to 99% of said pore former has a particle size of up to 350 μm and 1 to 50% by weight of said pore former has a particle size between 350 and 800 μm.

4. The gold-bearing preparation according to claim 3, wherein 65 to 75% by weight of said pore former has a particle size of up to 350 μm and 25 to 35% by weight of said pore former has a particle size of 350 to 700 μm.

5. The gold-bearing preparation according to claim 1, wherein said pore former has a spherical form.

6. A method of producing ductile, highly porous coatings on parts in dental technology, comprising sintering the gold-bearing preparation according to claim 1 at 700°–1050° C. on an appropriate metallic surface.

7. The gold-bearing preparation according to claim 1, wherein said pore former is present in amounts of 3 to 7% by weight.

8. The gold-bearing preparation according to claim 1, wherein said wax powder is dental-wax powder.

* * * * *